United States Patent

Nyo et al.

[11] Patent Number: 5,951,461
[45] Date of Patent: Sep. 14, 1999

[54] IMAGE-GUIDED LARYNGOSCOPE FOR TRACHEAL INTUBATION

[76] Inventors: Tin Nyo, 1615 Briggs Chaney Rd., Silver Spring, Md. 20905; Glenn Zaw-Mon, 14108 Greencroft La., Cockeysville, Md. 21030

[21] Appl. No.: 08/986,205

[22] Filed: Dec. 5, 1997

Related U.S. Application Data

[60] Provisional application No. 60/033,583, Dec. 20, 1996.

[51] Int. Cl.$^6$ .................................................. A61B 1/04
[52] U.S. Cl. ........................................ 600/118; 600/117
[58] Field of Search .................................. 600/117, 118, 600/120, 160, 183, 185, 188, 194; 348/65

[56] References Cited

U.S. PATENT DOCUMENTS

| | | |
|---|---|---|
| 4,651,746 | 3/1987 | Wall . |
| 4,910,590 | 3/1990 | Gillies et al. . |
| 5,018,509 | 5/1991 | Suzuki et al. . |
| 5,172,225 | 12/1992 | Takahashi . |
| 5,188,111 | 2/1993 | Yates et al. . |
| 5,203,320 | 4/1993 | Augustine . |
| 5,235,970 | 8/1993 | Augustine . |
| 5,257,636 | 11/1993 | White . |
| 5,307,804 | 5/1994 | Bonnet . |
| 5,331,967 | 7/1994 | Akerson . |
| 5,347,987 | 9/1994 | Feldstein et al. . |
| 5,400,771 | 3/1995 | Pirak et al. . |
| 5,506,912 | 4/1996 | Nagasaki et al. . |

*Primary Examiner*—Beverly M. Flanagan
*Attorney, Agent, or Firm*—Browdy and Neimark

[57] ABSTRACT

The invention relates to endotracheal intubation by an endoscope of the type that is automatically guidable in three dimensions in response to control signals. The endoscope has fiber optics and a TV camera for internal viewing. The TV image signals are processed to determine the geometrical shape of body parts near the tip of the endoscope. When the program determines that the vocal cords are in view, it guides the tip of the endoscope toward it and then into the trachea by sending control signals to the mechanical endoscope motion devices.

13 Claims, 7 Drawing Sheets

IMAGE-GUIDED LARYNGOSCOPE FOR TRACHEAL INTUBATION

This application claims benefit of Provisional Appln. 60/033,583 filed Dec. 20, 1996.

FIELD OF THE INVENTION

The present invention relates to an apparatus and method for inserting an oral tracheal airway into the trachea.

BACKGROUND OF THE INVENTION

Tracheal intubation with an oral airway (oral tracheal airway) for ventilation of a patient's lungs is an operation of critical importance. An incorrect intubation, in which the airway is inserted into the oesophagus instead of the trachea, will result in anoxia, brain damage, and death as air fails to reach the lungs. The patient s lungs are completely cut off from oxygen if the airway is wrongly inserted.

Correct intubation is so important that only an anesthesiologist or pulmonologist is allowed to perform it, even though the operation is actually a very simple one. As a result, patients who needed an immediate tracheal intubation have died while waiting for a specialist physician to arrive. Even though tests are available to indicate incorrect intubation (for example, testing for exhaled carbon dioxide, or measuring blood oxygenation) there is still grave danger.

One conventional intubation techniques uses a fiber-optic bronchoscope. Conventional intubation with a fiber-optic bronchoscope is pictured in the videotape "The Difficult Airway, Part III—Fiberoptic Intubation" from the American Society of Anesthesiologists, which is incorporated herein by reference as non-essential material.

First, an airway intubator is inserted through the mouth; it reaches to the back of the mouth area near the soft palate. The airway intubator is basically a relatively rigid, curved plastic tube. Its inner diameter is large enough to accept both an endotracheal tube and, within that, the fiber-optic bronchoscope. The endo-tracheal tube is a more flexible plastic tube through which the lungs will eventually be ventilated. The fiber-optic bronchoscope is smaller across than the inside diameter of the endo-tracheal tube.

The fiber-optic bronchoscope is inserted into the endotracheal tube outside of the patient, and then the physician guides the fiber-optic bronchoscope through the airway intubator and thence through the vocal cords. The fiber-optic bronchoscope is inflexible enough that its tip can be manipulated inside the patient by the physician's twisting and bending the protruding proximal portion. The fiber-optic bronchoscope may include an eyepiece for viewing, or may be connected to a TV monitor.

Fiber-optic technology is disclosed by Pirak et al, U.S. Pat. No. 5,400,771, and by Feldstein et al, U.S. Pat. No. 5,347,987, both of which are incorporated herein by reference in their entireties. The fiber optic bundle, including fibers for both image transmission to the TV camera and light transmission into the oral opening, are attached to the airway.

Pirak et al at column 4, lines 63–68, discloses that the physician can manipulate a fiber-optic member 12 while watching the image on a TV monitor.

Some endoscopes of the type incorporating fiber optics also include guide or control wires that allow the curvature of the endoscope to be varied. The controls can be activated either by hand turning of knobs or by automatic adjustment with solenoids, stepper motors, and so on, of the same type of controls. Conventional endoscope controls may also include automatic feed mechanisms that advance or retract the tip of the endoscope.

The incorporated Feldstein et al patent shows automatic control of a fiber-optic device by controls labeled 18 and 20. Television cameras have been connected to computers. The Feldstein patent discloses a computer digitizing the TV image from an endoscope fiber bundle and using the digitized image to detect motion of the endoscope away from a fixed position. Wire-controlled endoscopes are commonly used in industrial applications.

This technology is also disclosed in the following U.S. patents dealing with medical applications, all of which are entirely incorporated herein by reference: U.S. Pat. Nos. 5,506,912 to Nagasaki et al; 5,492,131 to Galel; 5,417,210 to Funda et al; and 5,018,509 to Suzuki et al.

Prior workers have used a computer to analyze the image from an endoscope and to control the position of the endoscope according to the computer's analysis of the image; but the programs they have developed are not at all suited to the task of tracheal intubation, and no automatic endotracheal intubation apparatus or method is now known.

As shown in the incorporated videotape, the tracheal opening, the larynx, presents a distinctive appearance: a strongly defined V-shape formed by the left and right vocal cords. No previous workers have used this distinctive shape, or any similar shape, for guiding an endoscope. Thus, the most distinctive aspect of the tracheal opening has been neglected by previous workers in the field.

For example, U.S. Pat. No. 4,910,590 to Gillies et al discloses automatic guidance of an endoscope according to illumination, distinguishing the center of a body tube (intestine) according dark and light ring-shaped areas in the image. Such image analysis would be useless in tracheal intubation.

The conventional techniques and apparatus have not overcome the problems of occasional incorrect intubation due to human error by physicians, or of intubations not being performed at all due to the absence of a qualified physician when needed. Even though the intubation is performed by a highly trained and experienced physician with the aid of a television and precise manual controls, incorrect intubations will always occur until automatic intubation guidance is provided to supplement or supplant human guidance.

SUMMARY OF THE INVENTION

Accordingly, the present invention has an object, among others, to overcome deficiencies in the prior art such as noted above.

The invention provides computer-guided tracheal intubation and an apparatus for accomplishing it; the computer guidance avoids human error and allows intubation to be performed by available medical personnel who are not pulmonologists or anesthesiologists.

The invention assembles conventional components, including a wire-guided fiberscope with a fiber-optic illuminating and imaging system, and a computer for digitizing the endoscopic image, and uses them for automatic guidance of a fiber-optic bronchoscope. The computer includes a program which identifies the patient's larynx and guides the fiber-optic bronchoscope between the vocal cords- After the fiber-optic bronchoscope is in place in the trachea, the endotracheal tube is moved forward over the fiber-optic bronchoscope, also entering the trachea, and then the fiber-optic bronchoscope may be withdrawn and the endo-tracheal tube connected to a respirator.

The program of the present invention utilizes the distinctive V-shape of the larynx vocal cords as a target. Such a target image is not only the best indication of the tracheal opening location, it is also easily analyzed by a computer program because it comprises two straight lines, which meet at a point. Thus both transverse and angular relations of the fiber-optic bronchoscope to the larynx are quite easily determined using algorithms adapted to simple, straight-line geometrical formulations.

As the fiber-optic bronchoscope of the invention is advanced through the airway intubator, only the smooth plastic interior of the intubator, and/or the tongue, is in view of the fiber-optic bronchoscope imaging head, and the computer will find no converging lines in the digitized image. Once the vocal cords of the larynx come into camera view, however, the computer is presented with the strong V-shape of the vocal cords, which the image-analysis program can identify. The strong V-shape comes about because the laryngeal opening is strongly illuminated once the distal end of the fiber-optic bronchoscope, with its light-transmitting fiber tips, comes close to the vocal cords; but the actual opening to the trachea constitutes a dark void, and shows up very dark in the image. Thus, the edges of the vocal cords are quite clearly defined. (The interior of the trachea is shiny and reflective as are the vocal cords, but since it is a space with a relatively small opening it appears dark, just like the inside of a box lined with aluminum foil when viewed through a small opening.)

The anatomy of the larynx includes many structures, some of which define generally straight lines as seen in endoscopic view: but only the inferior (true) vocal cords have the distinctive appearance which the program of the present invention selects. In particular, the oesophagus completely lacks the appearance of the vocal cords—and oesophageal intubation is the danger to be avoided.

The vocal cord opening, the rima glottidis, is bounded at the anterior end by the true or inferior vocal cords, which as noted form two sharply defined lines meeting at an apex point on the anterior side; at the ends opposite the apex, on the posterior side, the true vocal cords are attached to the vocal processes of the base of the arytenoid cartilages. The arytenoids are moved by a muscle to vary the tension on the vocal cords. A mucus membrane passes between the bases of the arytenoid cartilages, forming a posterior border to the rima glottidis. The rima glottidis thus has, overall, the shape of an isosceles triangle, with two longer legs being the left and right true vocal cords and the base being the membrane of the arytenoid. The vocal cords are 20–25 mm long in males and 15–21 mm long in females; the base is about 8 mm long. The included angle at the apex is thus only about 10–15 degrees.

According to Gray's Anatomy (Bounty Books, N.Y.), incorporated herein as non-essential material, the shape of the rima glottidis when at rest (as in quiet respiration) is very nearly triangular as described above. However, even when not at rest the shape may still be still triangular. For example, when a high note is sounded by the voice the vocal cords are drawn together, but there is still a triangular opening at their posterior end. During forced inhalation the shape becomes diamond or lozenge-shaped. The shape to be expected during intubation is of course the isosceles triangular shape of the rima glottidis at rest or during vocalization.

The oesophagus or gullet is to be avoided since if the endo-tracheal tube is mistakenly inserted into the gullet, the patient's stomach will be ventilated instead of the lungs, leading to serious danger. The gullet opening is located immediately adjacent the larynx in the pharyngeal region.

Thus, the task of the computer program in the present invention is to identify the rima glottidis and guide the distal end of the fiber-optic bronchoscope through it, while avoiding the oesophagus and other structures located nearby. The program of the present invention does this by finding the apex of the vocal cords at the anterior end of the rima glottidis and guiding the fiber-optic bronchoscope into the trachea using the apex as a benchmark; it avoids the gullet opening because this opening lacks the distinctive triangular shape of the rima glottidis.

Program and computational methods for digitizing the image from the fiber-optic bronchoscope are well-known, and sub-programs for determining the location of a line, like that defined by an edge of a vocal cord, are also well-known. Therefore, subprograms of the main program of the invention can easily find, and determine the positions of, the left vocal cord edge, the right vocal cord edge, and their junction point or anterior apex.

Moreover, an approximately straight line, such as an edge of a vocal cord, can be analyzed and approximated as a mathematical line, if desired.

Thus, once the vocal cords are in view, the data from the fiber-optic bronchoscope camera image can be analyzed according to well-known computational techniques to generate an idealized V-shape corresponding in all pertinent aspects—transverse X and Y location, included V angle, and relative angle (i.e., due to rotation of the fiber-optic bronchoscope within the oral cavity) to the vocal cords as they stand in relation to the distal end of the fiber-optic bronchoscope.

Moreover, since the rima glottidis is essentially triangular, the size of the idealized image can also be made comparable to the size of the actual vocal cords as perceived from the imaging point of the distal end of the fiber-optic bronchoscope. This allows the axial distance of the fiber-optic bronchoscope tip from the opening to be ascertained.

In summary, the invention does three things: first, it ascertains whether or not the vocal cords are in view, and therefore are near the distal (imaging) end of the fiber-optic bronchoscope; second, it determines the position of the distal end relative to the vocal cord opening (the rima glottidis); third, it guides the distal end through the vocal cord opening.

In a preferred embodiment the guidance is accomplished by comparing the digitized image of the rima glottidis (camera image) to a stored data which corresponds to the image of the rima glottidis when the fiber-optic bronchoscope is poised in the correct position to go directly into the trachea when advanced (reference image). The position might be specified in terms of: X-location of the anterior vocal cord apex (e.g. left-to-right on a TV monitor displaying the fiber-optic bronchoscope image) and Y-location (up-and-down on the same monitor) of the apex (intersection point of the lines of the left and right vocal cords); Z-location according to size of the rima glottidis triangle, corresponding to the nearness of the fiber-optic bronchoscope tip to the vocal cords (or zoom, if the fiber-optic bronchoscope were to include a tip lens with zoom capability); and X-location or Y-location of the centroid of the image triangle. These may be corrected, in various orders, to gradually bring the fiber-optic bronchoscope tip to the poised position where it may advance into the trachea.

As an alternative to comparison with a triangle in memory the digitized image can be analyzed mathematically to determine the position of the centroid of the rima glottidis, and guide the fiber-optic bronchoscope tip directly in. Also, the isosceles triangle need not be determined; just the apex and the two lines are enough to guide the fiber-optic bronchoscope tip into the trachea. This can be done by maintaining a constant angle between the optical axis of the fiber-optic bronchoscope tip (i.e. the center of the image on a monitor screen) and the apex.

The program of the present invention is preferably adapted to the particular mechanical controls of the fiber-optic bronchoscope. The fiber-optic bronchoscope will generally include one control for Z-axis motion, defined herein as advance and withdrawal of the fiber-optic bronchoscope tip as the length is changed. The other two directions of lateral motion may be variously defined.

Some wire-controlled endoscopes are controllable in two directions, which might be designated as X and Y. Other devices will contain just one wire (or two opposed wires) and be subject to bending control in only one direction. In these devices the third direction of control is via a rotation of the fiber-optic bronchoscope, that is, rolling about the longitudinal axis of the fiber-optic bronchoscope as it passes through the control unit.

In the case where direct lateral control of the tip is available in two orthogonal directions, such as up-down and left-right, the guidance portion of the tip control algorithm will be straight-forward. If one later direction plus rolling are available, then full control is still available since three degrees of freedom are provided, but the control program will be less straight-forward. Rotation of the image will also involve translation.

A monitor is optionally provided to show medical personnel the progress of the fiber-optic bronchoscope. If desired an override or kill switch can be included to stop the program if any abnormality or scar exists which might cause the fiber-optic bronchoscope tip to go off-course; and manual over-ride control of the fiber-optic bronchoscope tip can be provided for cases where the program fails for some reason.

BRIEF DESCRIPTION OF THE DRAWING

The above and other objects and the nature and advantages of the present invention will become more apparent from the following detailed description of an embodiment taken in conjunction with drawings, wherein.

DETAILED DESCRIPTION OF THE PREFERRED EMBODIMENT

Here, and in the following Claims:

"Endoscope" means any elongated device including some means for transmitting an image from a distal end to a proximal end, such that the image may be viewed by a person or registered by a computer from the proximal end; such means can include a fiber optic bundle, but is not limited to a fiber optic bundle; for example, video transmission from a small camera would be within the scope of this term.

"Bronchoscope" means an endoscope adapted to viewing the trachea or able to view the trachea of a patient.

"Controllable endoscope" means an endoscope which can be controlled from its proximal end, or a point adjacent its proximal end, to adjust the position, angle, or velocity of its imaging distal end.

"Computer storage medium" means any built-in device such as a hard drive, any portable device such as a floppy disk or magnetic tape, and any built-in solid-state or chip storage such as ROM, RAM, and so on, and including CPU memory.

"X" means one direction which is perpendicular to the length of the fiber-optic bronchoscope, either at the distal tip or elsewhere.

"Y" means the same as "X", one direction which is perpendicular to the length of the fiber-optic bronchoscope; but X and Y are not parallel, and are preferably perpendicular to one another as well as being both perpendicular to the fiber-optic bronchoscope, so that if X and Y motion is provided then the tip can move over a surface by means of the X and Y controls.

"Z" means generally parallel to the length of the fiber-optic bronchoscope, either at the distal tip or elsewhere.

"θ" means an angular rotation about the length of the fiber-optic bronchoscope, either at the distal tip or elsewhere.

Figure 1:
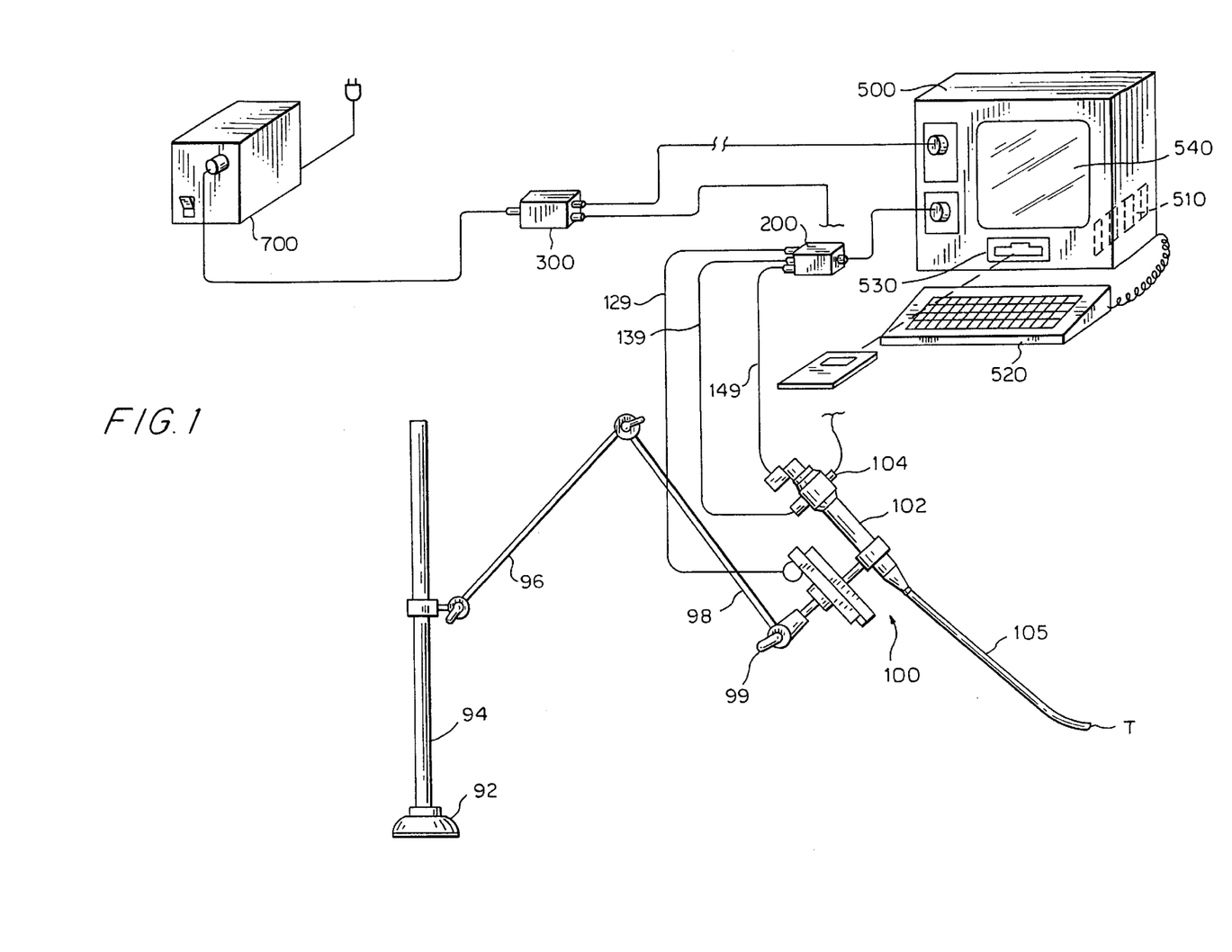
FIG. 1 is a perspective view of the invention.

FIG. 1 is an overview of a preferred embodiment of the present invention. A fiber-optic bronchoscope 10 is held by a base 92, stand 94, arms 96 and 98, and adjustable clamp 99, all supporting a stage 100 which includes elements for manipulating the distal tip T of the bronchoscope 10 for intubation into the mouth of the patient (not shown). The bronchoscope 10 includes a housing 102 and imaging means such as a lens at the distal tip T of a fiber-optic bundle 105 passing the image through the bundle 105. (The internal parts are not shown; this structure is conventional and is shown in the incorporated patents.) The bronchoscope also includes a conventional CCD camera and optical means for illuminating inside the patient from a remote lamp 700.

A computer 500 is provided, preferably with a video display screen or monitor 540, keyboard 520, and floppy drive 530 for accepting a diskette 532. The endoscopic image from the tip T is optionally displayed on the screen 510. A program for controlling the fiber-optic bronchoscope 10 resides in memory 510, to which it may be loaded from the diskette 532 (or equivalent digital storage medium such as a tape, laser disc, etc.). The computer 500 can be replaced with a dedicated microprocessor, hard-wired circuit, custom chip, or other equivalent device with a fixed program.

Standard power/video connectors 200 and 300 interconnect the bronchoscope 10, computer 500, lamp 700, and the various controls of the stage 110 as needed for transmitting illuminating light, video image signals, stage manipulation commands, and so on. Connector boxes may include signal amplifiers for driving control motors of the stage 100, A/D or D/A converters, power supplies or batteries, and other conventional accessories.

Figures 2, 3:
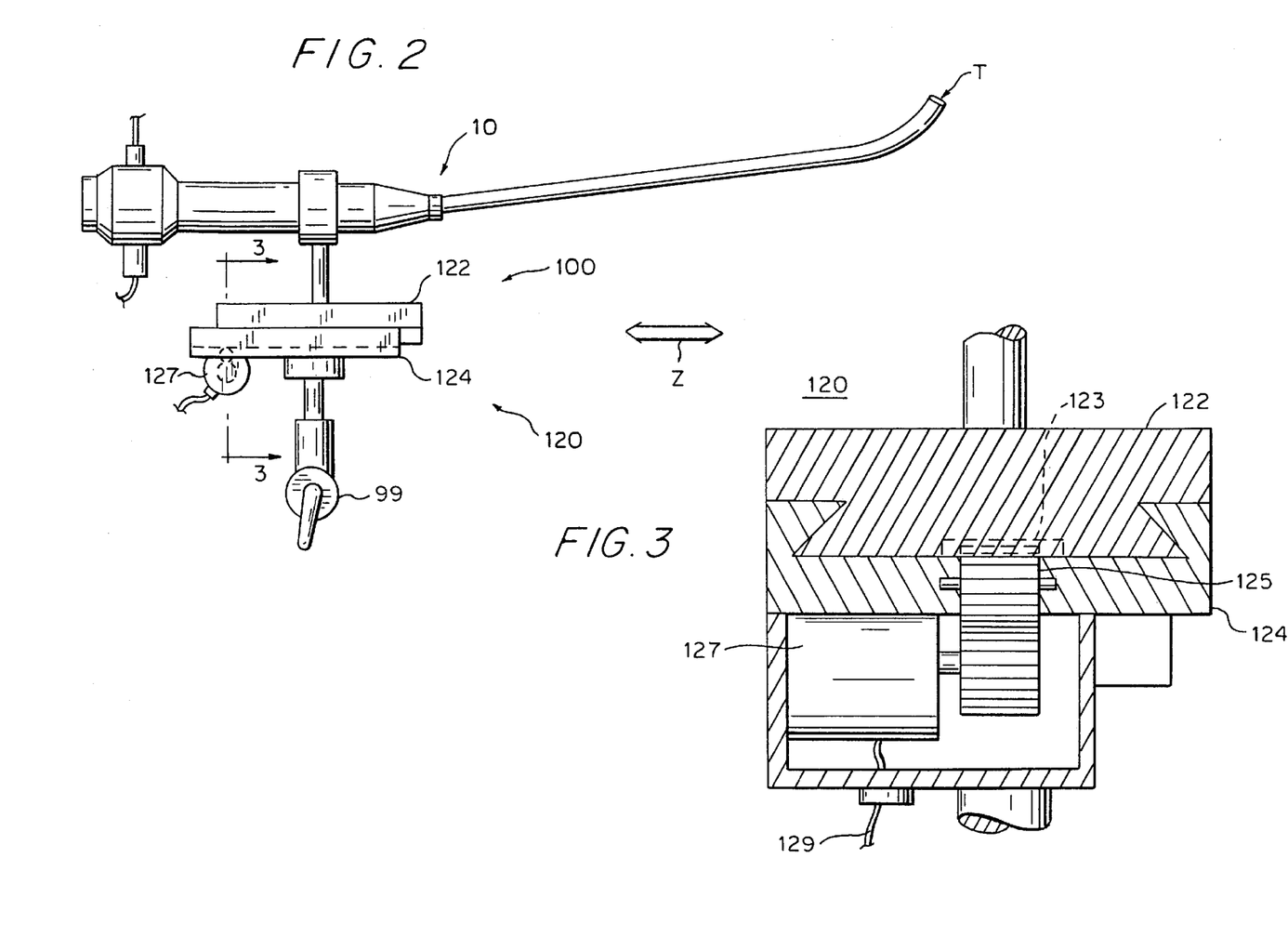
FIG. 2 is an elevational view of the fiber-optic bronchoscope and stage.
FIG. 3 is cross-sectional view taken along line 3—3 of FIG. 2, showing the mechanism for Z-axis motion.

FIGS. 2 and 3 show in greater detail the portions of the stage 100 devoted to Z-axis translational motion (the direction is indicated by the arrow Z in FIG. 2), which are generally labeled 120. These include an upper slider 122 and a lower slider or base 124 mutually slidable in the Z direction. The upper slider 122 includes a rack of gear teeth 123 and the lower slider houses a gear train including a pinion gear 125 engaging the rack 123. The gear train is connected to a motor 127 accepting control signals through a wire 129.

Figure 4:
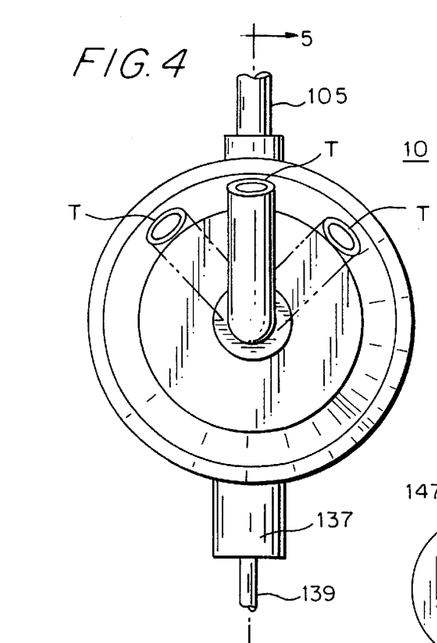
FIG. 4 is a perspective view of the fiber-optic bronchoscope motion unit looking along the Z-axis from a point adjacent the fiber-optic bronchoscope tip.
Figure 5:
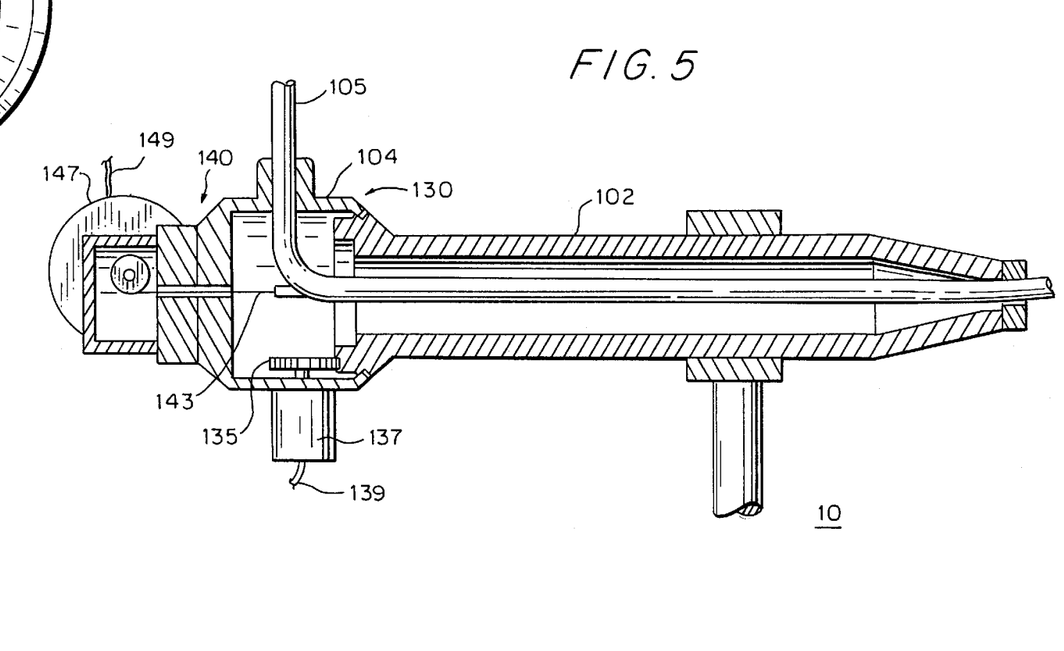
FIG. 5 is a cross-sectional view taken along line 5—5 of FIG. 4.

FIGS. 4 and 5 show in greater detail those parts of the stage 100 used for rotation of the fiber-optic bronchoscope 10 about the θ-axis, generally labeled 130, and for laterally diverting the tip T in an X-direction, generally labeled 140.

The θ-axis motion mechanism 130 rotates the bundle 105 within the housing 102 by rotating a rear portion 104 of the housing with a gear 135 driven by a motor 137 accepting drive signals from a wire 139. FIG. 4 shows in two phantom views alternative positions of the tip T due to rotation of the bundle 105 around the θ-axis.

The X-axis drive 140 includes a control wire 149 and a motor or step-motor 147 that adjusts the length of a wire 143 which runs into the bundle 105. Held within the bundle casing, it runs up to the tip T through a flexible portion adjacent to the tip, and is the means for moving the tip up or down. This wire control, which is conventional, is analogous to control of a finger by tendons.

FIGS. 6A–6D illustrate the control program of the invention, which in the illustrated exemplary embodiment may reside in the memory 510.

Figure 6A:
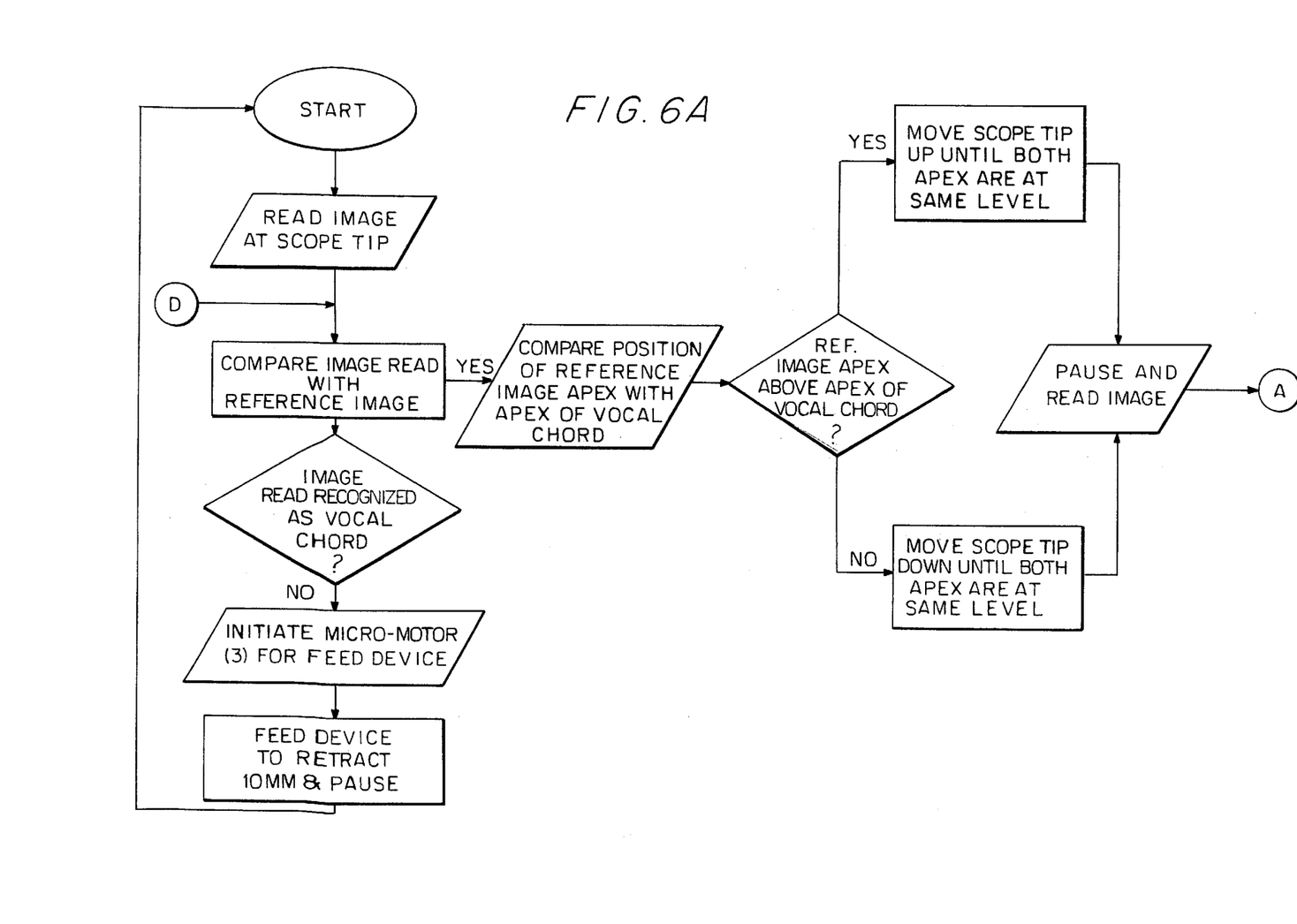
FIGS. 6A–6D are schematic views showing a preferred embodiment of the program of the invention.

In FIG. 6A the program begins by receiving (and digitizing if not already done) the camera image of the patient from the tip T, and comparing the camera image with a previously stored reference image, using conventional subroutines for image comparison. If the camera image is not recognized as the vocal cords or rima glottidis triangle (see the discussion above in the Summary), the Z-drive is activated to advance the fiber-optic bronchoscope 10 mm and then pause. If the rima glottidis is recognized, then the program locates the apex of the rima glottidis triangle in the camera image. The positions of the apices of the camera and reference images are compared to determine whether the apex of the reference image is "above" that of the camera image. (The word "above" may or may not refer to the vertical direction of the camera image as seen on the monitor screen 540; in the illustrated embodiment it actually refers to the direction in which the tip T is displaced from the straight-line extension of the bundle 105.) If the reference image is "above", then the tip T is moved in the X-direction by means of the program activating the motor 147 through wire 149 to bring the triangle apices together; conversely, if it is below then the tip T is moved in the opposite X-direction, likewise to bring the apices to the same level.

If the vocal cords are not recognized, the program advances the tip T 10 mm and then pauses to re-analyze the camera image and again attempt to recognize it.

Figure 6B:
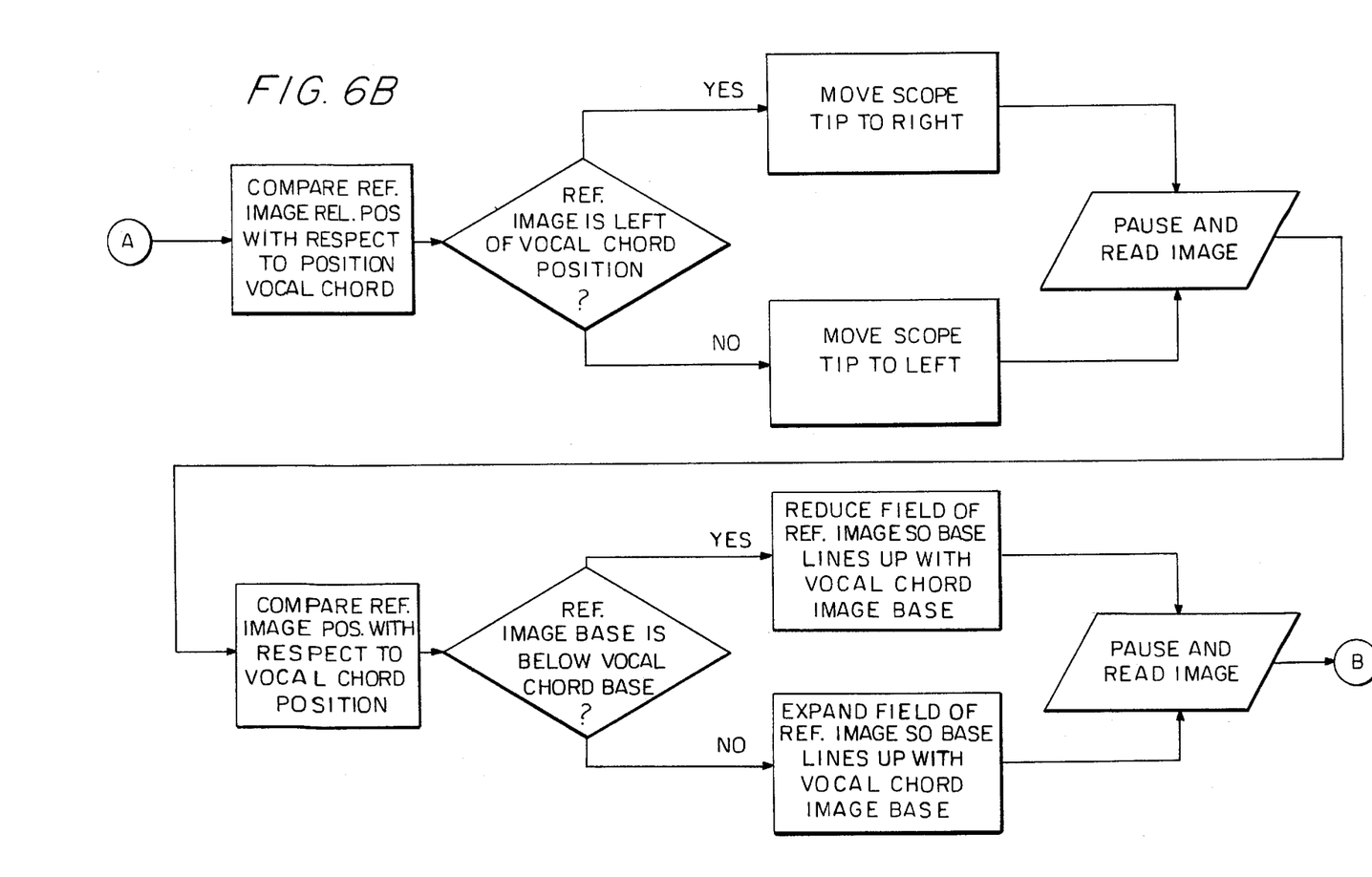

The program pauses to read the image again, and then proceeds (to "A" in FIGS. 6A and 6B). Referring to FIG. 6B, the relative positions of the camera and reference apices are again compared, but this time as to their relative displacement in a "left-right" or Y-direction, which is transverse to the X-direction already adjusted. In the illustrated embodiment, the Y-direction position of the apex of the camera image is adjusted by rotating the bundle 105 about the θ-axis. This can be understood in reference to FIG. 4, in which the X-direction motion of the tip T is radially inward or outward and a transverse motion of the tip T is obtained by rotational motion, i.e. θ motion.

However, a rotation of the bundle 105 also automatically rotates the camera image, and thus can bring the two rima glottidis triangles—camera and reference—into angular alignment with the respective base of each at the same angle relative to the respective apex. The program rotates the image until this alignment occurs.

FIG. 6B shows that, after the "left-right" displacement of the tip is adjusted and the rima glottidis triangles are similarly situated, the program again pauses to read the image and then compares the sizes of the camera and reference images with respect to position of the vocal cord image. If the base of the reference rima glottidis triangle is below the base in the cameral image, the field is reduced; if not, it is expanded. In other words, the camera image is "zoomed" to expand or contract. This is accomplished by moving the tip in the Z-direction by appropriate control signals over the wire 129 to the motor 127 until the camera and reference triangles are the same size.

Figure 6C:
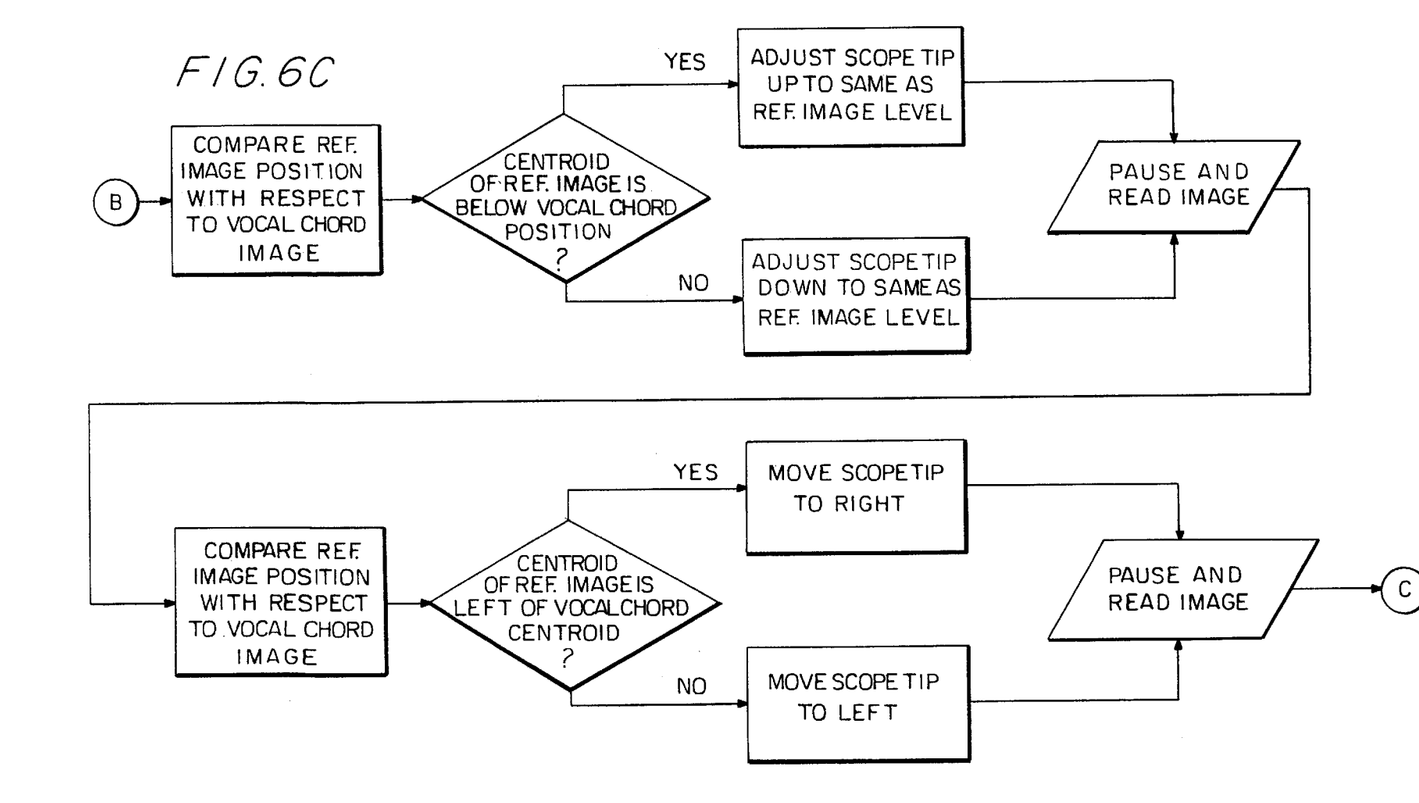

The program then proceeds to point "B", connecting to FIG. 6C. In this portion of the program the centroids of the camera and reference images are compared and brought into coincidence by adjusting the tip T in the X-direction, (by control signals on the wire 149 to the motor 147 to adjust the internal wire 143 of the bundle 105), in the "up/down" direction. After a further pause the centroids of the images are again brought into coincidence in the "left/right" direction by rotating the bundle 105 in the θ-direction.

Figure 6D:
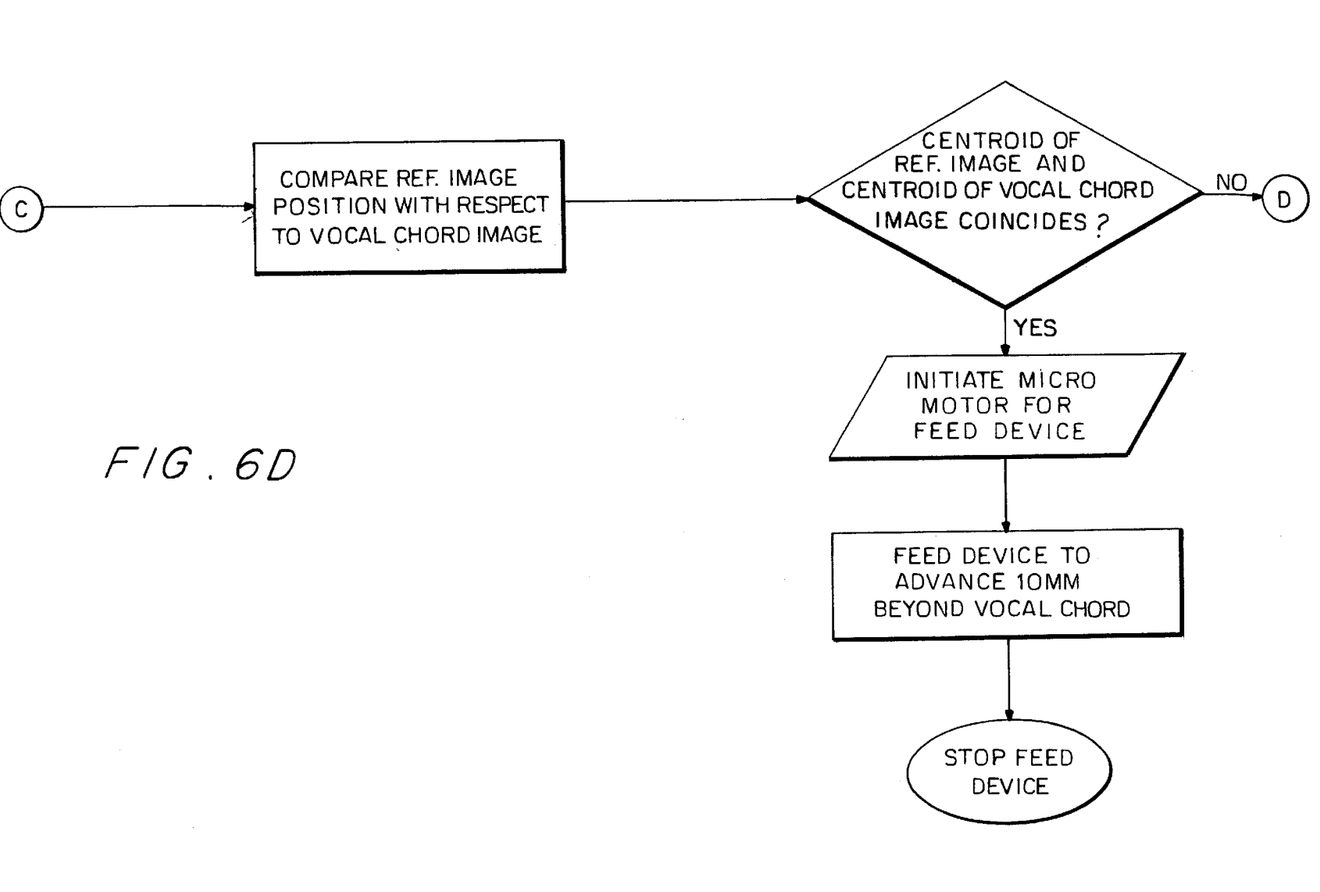

FIG. 6D continues where FIG. 6C left off at "C", with the following program portion. In this final operational step the positions of the centroid of the camera image of the rima glottidis and the centroid of the reference image of the rima glottidis are compared. If they are coincident (within a predetermined distance of each other) then the program proceeds with insertion of the fiber-optic bronchoscope into the trachea by activating the Z-direction drive motor 127 to advance 10 mm past the vocal cords and then stops. If they are not coincident the program returns to "D" in FIG. 6A.

Other embodiments and programs, not illustrated, are possible and fall within the scope of the invention. The gist of the invention is computer recognition of the geometrical shape of a body part from an endoscope image, particularly an orifice, and automatic advance of the endoscope tip into the orifice or up to the body part; or computer-controlled automatic advance and guidance of an elongated member having an imaging device at its tip, through a body orifice locatable by linear elements. The present invention thus encompasses related automatic guidance, such as automatically guiding a catheter toward and through a tri-cuspid or bi-cuspid heart valve, which appears as a set of lines converging to a central apex. The invention also includes imaging with non-visible light such as infrared or ultraviolet, and imaging with sonic waves.

The invention includes the provision of more than three degrees of freedom. For example, it includes provision of both X and Y lateral wire control and also θ-rotation. It also includes an endoscope which advances sinuously, in the manner of a snake, such that a steady curve shape is maintained even while the bronchoscope advances or retreats along the curve. The invention also contemplates guidance of a rigid curved fiber-optic bronchoscope into the trachea, using only advance and retreat at the holder and angular changes of the holder.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation.

The industrial applicability is in tracheal intubation. The problem solved by the invention is that highly skilled personnel have been required for endotracheal intubation.

What is claimed is:

1. A system for intubation of a person having internal body parts, the system comprising:
   (a) an endoscope having a tip and including optical means to view the internal body parts;
   (b) a camera, coupled to said endoscope, producing electronic image signals;
   (c) mechanical means, responsive to control signals, for moving said endoscope tip in three dimensions; and
   (d) processing means, inputting said image signals and outputting said control signals, for guiding said endoscope tip to a predetermined three-dimensional spatial position in relation to a predetermined one of the body parts, said processing means comprising
      analyzing means for analyzing said image signals to determine a distinctive geometrical shape of a viewed body part;
      determining means for determining whether the distinctive geometrical shape is that of the predetermined body part; and
      moving means for moving the tip to the predetermined spatial position.

2. The system according to claim 1, wherein said predetermined body part includes an orifice and wherein the processing means is for guiding said tip through the orifice.

3. The system according to claim 2, wherein the predetermined body part is the person's rima glottidis and said processing means is for guiding the tip into the person's trachea to a position which is a predetermined distance beyond the rima glottidis.

4. The system according to claim 1, wherein said processing means includes a programmable digital computer and a program adapted to be run on said computer, and said program includes said determining means.

5. The system according to claim 4, wherein said program further includes said analyzing means.

6. The system according to claim 4, wherein said program further includes said moving means.

7. The system according to claim 1, wherein the determining means includes means for comparing a digitized image of the predetermined body part to stored data.

8. The system according to claim 1, wherein the determining means includes means for performing mathematical analysis.

9. A method for intubation of a person using a system in accordance with claim 1, comprising:
   placing the endoscope tip at the entrance of the body part to be intubated;
   engaging said camera, processing means and mechanical means to automatically guide the tip of the endoscope to a predetermined spatial position in relation to a predetermined body part.

10. A method according to claim 9, wherein said predetermined body part is the person's rima glottidis and said placing step comprises placing the endoscope tip in the person's mouth near the entrance to the trachea.

11. A computer program embodied on a computer-readable storage medium to control a system comprising:
   (a) an endoscope having a tip and including optical means to view internal body parts;
   (b) a camera, coupled to said endoscope, producing electronic image signals;
   (c) mechanical means, responsive to control signals, for moving said endoscope tip in three dimensions; and
   (d) a processor;
   wherein the program inputs said image signals and outputs said control signals, for guiding said endoscope tip to a predetermined three-dimensional spatial position of said tip in relation to a predetermined body part, by
      analyzing said image signals to determine a distinctive geometrical shape of a viewed body part;
      determining whether the distinctive geometrical shape is that of the predetermined body part; and
      outputting control signals to direct said mechanical means to move said tip to the predetermined spatial position.

12. The computer storage medium according to claim 11, wherein said program further includes said analyzing means.

13. The computer storage medium according to claim 11, wherein said program further includes said moving means.

* * * * *